(12) United States Patent
Mueller

(10) Patent No.: US 10,058,406 B2
(45) Date of Patent: Aug. 28, 2018

(54) NOZZLE FOR BLASTING LIQUID DETERGENTS WITH DISPERSED ABRASIVE PARTICLES

(75) Inventor: Daniel Mueller, Burgstall (IT)

(73) Assignee: Dental Care Innovation GmbH, Röttenbach (DE)

( * ) Notice: Subject to any disclaimer, the term of this patent is extended or adjusted under 35 U.S.C. 154(b) by 615 days.

(21) Appl. No.: 13/520,749

(22) PCT Filed: Jun. 10, 2011

(86) PCT No.: PCT/IB2011/001325
§ 371 (c)(1),
(2), (4) Date: Jul. 5, 2012

(87) PCT Pub. No.: WO2012/069894
PCT Pub. Date: May 31, 2012

(65) Prior Publication Data
US 2013/0288195 A1    Oct. 31, 2013

(30) Foreign Application Priority Data

Nov. 12, 2010    (DE) .................. 10 2010 051 227

(51) Int. Cl.
| A61C 17/00 | (2006.01) |
| B05B 1/34 | (2006.01) |
| B24C 5/04 | (2006.01) |
| B05B 15/18 | (2018.01) |
| A61C 3/025 | (2006.01) |

(52) U.S. Cl.
CPC .......... *A61C 17/005* (2013.01); *B05B 1/3415* (2013.01); *B05B 15/18* (2018.02); *B24C 5/04* (2013.01); *A61C 3/025* (2013.01)

(58) Field of Classification Search
CPC ........ B24C 5/04; B05B 1/3415; A61C 17/005
USPC .................................... 451/102; 433/88, 216
See application file for complete search history.

(56) References Cited

U.S. PATENT DOCUMENTS

| 2,647,799 | A | * | 8/1953 | Kinney | ................. | B05B 1/3415 |
| | | | | | | 138/37 |
| 2,999,648 | A | * | 9/1961 | Wahlin | ................. | B05B 1/3415 |
| | | | | | | 239/463 |
| 3,666,183 | A | * | 5/1972 | Smith | .................. | B05B 1/3405 |
| | | | | | | 239/463 |
| 4,247,049 | A | * | 1/1981 | Gailitis | ................ | B05B 1/3415 |
| | | | | | | 239/497 |
| 4,252,768 | A | | 2/1981 | Perkins et al. | | |

(Continued)

FOREIGN PATENT DOCUMENTS

| EP | 0258242 B1 | 4/1989 |
| EP | 0476632 A2 | 3/1992 |

(Continued)

OTHER PUBLICATIONS

International Search Report in corresponding PCT/IB2011/001325 (four pages).

*Primary Examiner* — Christopher M Koehler
*Assistant Examiner* — Henry Hong
(74) *Attorney, Agent, or Firm* — Hooker & Habib, P.C.

(57) ABSTRACT

For to avoid clogging from abrasive media, a nozzle contains an element for circular vortexing the passing jet of detergents in combination with a defined flexibility of its elements, which—together with a pulsating stream of media—causes vibrations, that constantly lead to peeling off adhering residues.

34 Claims, 1 Drawing Sheet

(56) References Cited

U.S. PATENT DOCUMENTS

Figure 1:
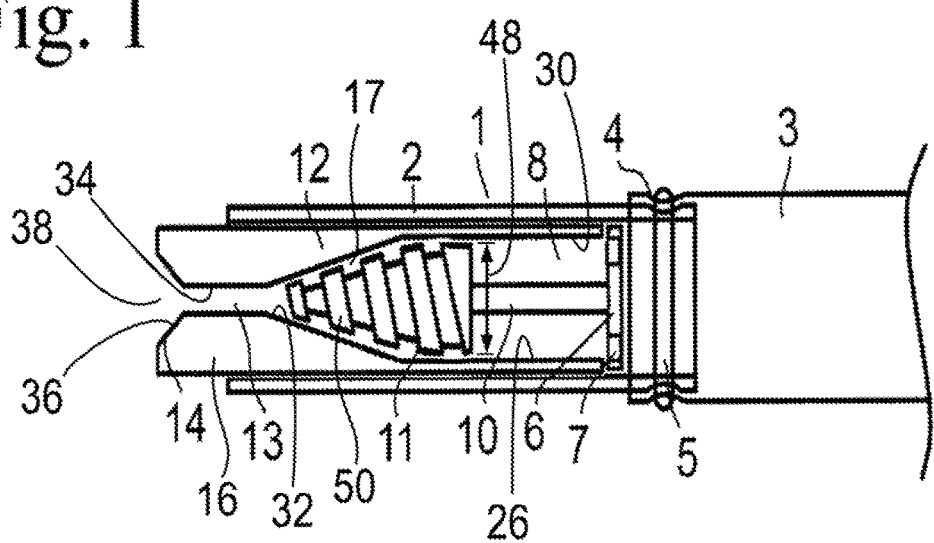

| | | | |
|---|---|---|---|
| 4,253,610 A | 3/1981 | Larkin | |
| 4,462,803 A | 7/1984 | Landgaf et al. | |
| 4,478,368 A | 10/1984 | Yie | |
| 4,482,322 A | 11/1984 | Hain et al. | |
| 4,494,698 A | 1/1985 | Brown et al. | |
| 4,540,365 A | 9/1985 | Nelson et al. | |
| 4,545,157 A | 10/1985 | Saurwein | |
| 4,595,365 A | 6/1986 | Edel et al. | |
| 4,608,018 A | 8/1986 | Ghedini et al. | |
| 4,611,759 A | 9/1986 | Cox | |
| 4,707,952 A | 11/1987 | Krasnoff | |
| 4,738,401 A * | 4/1988 | Filicicchia | B05B 1/3415 239/487 |
| 4,776,794 A | 10/1988 | Meller | |
| 4,954,688 A | 8/1990 | Yie | |
| 4,979,679 A | 12/1990 | Downs | |
| 5,018,317 A | 5/1991 | Kiyoshige et al. | |
| 5,052,624 A | 10/1991 | Boers et al. | |
| 5,056,718 A | 10/1991 | Wakefield | |
| 5,094,615 A | 3/1992 | Bailey | |
| 5,114,766 A | 5/1992 | Jacques | |
| 5,169,065 A | 12/1992 | Bloch | |
| 5,186,625 A | 2/1993 | Bailey | |
| 5,203,968 A | 4/1993 | Henricson | |
| 5,219,897 A * | 6/1993 | Murray | A61B 17/8833 433/228.1 |
| 5,226,565 A | 7/1993 | Hladis et al. | |
| 5,236,971 A * | 8/1993 | Murray | A61B 17/8833 433/201.1 |
| 5,312,040 A | 5/1994 | Woodward | |
| 5,335,459 A | 8/1994 | Dale | |
| 5,385,304 A | 1/1995 | Haruch | |
| 5,390,450 A * | 2/1995 | Goenka | B24C 1/003 451/102 |
| 5,551,909 A | 9/1996 | Bailey | |
| 5,553,784 A | 9/1996 | Theurer | |
| 5,558,474 A | 9/1996 | Wildon | |
| 5,595,346 A | 1/1997 | Haruch et al. | |
| 5,601,478 A | 2/1997 | Mesher | |
| 5,641,368 A | 6/1997 | Romes et al. | |
| 5,733,174 A | 3/1998 | Bingham et al. | |
| 5,746,596 A | 5/1998 | Gallant et al. | |
| 5,857,851 A | 1/1999 | Chavanne | |
| 5,857,900 A | 1/1999 | Shank, Jr. | |
| 5,918,817 A | 7/1999 | Kanno et al. | |
| 5,921,456 A | 7/1999 | Kirsch et al. | |
| 6,077,152 A | 6/2000 | Warchime | |
| 6,119,964 A | 9/2000 | Lombari | |
| 6,283,833 B1 * | 9/2001 | Pao | B24C 5/04 451/102 |
| 6,394,366 B1 * | 5/2002 | Adams | B05B 1/3447 239/463 |
| 6,485,304 B2 | 11/2002 | Beerstecher et al. | |
| 6,561,440 B1 * | 5/2003 | Hofherr | B05B 1/3478 239/472 |
| 6,601,783 B2 | 8/2003 | Chisum et al. | |
| 6,688,947 B2 | 2/2004 | Anand et al. | |
| 6,695,686 B1 * | 2/2004 | Frohlich | B24C 1/003 239/433 |
| 6,752,685 B2 | 6/2004 | Ulrich et al. | |
| 6,824,453 B1 | 11/2004 | Andersson | |
| 6,837,709 B2 | 1/2005 | Sierro et al. | |
| 6,846,211 B2 | 1/2005 | Yasuda et al. | |
| 6,935,576 B2 | 8/2005 | Hara | |
| 6,964,569 B2 | 11/2005 | Nordmo et al. | |
| 7,757,971 B2 | 7/2010 | Hall et al. | |
| 7,762,812 B2 | 7/2010 | Pichat et al. | |
| 2004/0125689 A1 | 7/2004 | Ehrfeld et al. | |
| 2004/0219483 A1 * | 11/2004 | Egeresi | A61C 17/0214 433/80 |
| 2009/0227185 A1 * | 9/2009 | Summers | E21B 7/18 451/39 |
| 2011/0306279 A1 * | 12/2011 | Hunziker | B24C 7/0023 451/102 |
| 2012/0282570 A1 * | 11/2012 | Mueller | A61C 3/025 433/88 |

FOREIGN PATENT DOCUMENTS

| | | |
|---|---|---|
| EP | 0526087 A1 | 2/1993 |
| EP | 0810038 B1 | 12/1997 |
| WO | 2004037109 A2 | 5/2004 |
| WO | 2011070385 A1 | 6/2011 |

* cited by examiner

NOZZLE FOR BLASTING LIQUID DETERGENTS WITH DISPERSED ABRASIVE PARTICLES

FIELD OF THE INVENTION

The present invention relates to a nozzle, that would not easily be clogged or worn out from abrasive media in a stream of detergents or water.

BACKGROUND OF THE INVENTION

Nozzles for shot-blasting with detergents, that contain abrasive media hitherto had diameters sized a multiple of that of the particles for to avoid clogging.

However, the abrasive effect of this cleaning method depends on the pressure of the cleaning fluid. This to one part depends on the power of the pressure pump, but as well on the compression ratio that results from the ratio between the gauges of inlet and ejecting orifices.

Not only for this reason as fine a nozzle as possible is preferred: A finer pressure jet also results in a more sharply contured cut or erosion, which usually is aimed at.

Contrary to systems, where air or a gas jet presses the abrasive components through a nozzle, as known with sand-blasting or shot-peening, or with the use of compressed gases as carriers for finer abrasive media—e.g. for dental cleaning—(see to U.S. Pat. Nos. 4,608,018, 4,540,365, 4,462,803, 4,482,322, 4,595,365, 5,094,615, 5,186,625, 5,558,474, 5,733,174, 5,746,596, 5,857,851, 5,857,900, 5,918,817, 6,485,304, 6,752,685, 6,837,709, 6,935,576 and 6,964,569), as well as on nozzles for blasting a combination of liquid and gas or compressed air, (as in U.S. Pat. Nos. 4,253,610, 4,776,794, 5,203,698, 5,385,304, 5,551,909, 5,553,784 and 5,595,346) the employment of insoluble particles mixed into liquid media as such is the main cause for blocking and thus the breakdown of such devices.

PRIOR ART

However, there are well-known measures, which can solve the problem to a certain degree: The classical paradigm is, to manufacture a nozzle with plain and smooth walls from materials, as hard as possible and resistant to wear and tear—i.e. highly compressed ceramics, rubies or diamonds—as found in EP 0.476.632 B1 in detail and also in U.S. Pat. Nos. 4,252,768, 4,545,157, 5,052,624 and U.S. Pat. No. 7,757,971.

One of the few exceptions to this is found in U.S. Pat. No. 4,494,698, similarly in U.S. Pat. No. 4,611,759, which describe a nozzle from PU, which there is offered for blasting with abrasive media, however is known to be applied only to sputter gypsum milk in exhaust ports of desulfurization plants.

On the other hand, superhard materials are expensive and their treatment is intricate, even if only implemented to the nozzle bore, or when lining their walls with it, as suggested in DE 3528137 A1 and U.S. Pat. No. 5,335,459.

A possible way to avoid the employment of superhard materials is to buffer the abrasive medium with a surrounding stream of other media, in order to prevent the wear of the nozzle walls, as suggested in EP 0258 242 B1 (claim 2), EP 0573 957 B1, U.S. Pat. Nos. 4,478,368, 4,707,952, 5,018,317, 5,601,478, 6,077,152, 6,824,453 and U.S. Pat. No. 6,846,211.

Other suggestions are ducting and smoothing the abrasive jet with lamella nozzles (DE 196 49 921, EP 0691 183 B1, U.S. Pat. No. 5,169,065) and/or guiding it in a laminar flow along the nozzles walls (DE 3622292 A1), or to reduce contact to it by an accelerated nuclear jet, that would keep it convergent within the tubular walls. (DE 19640921 c1 and U.S. Pat. No. 5,056,718).

However, inevitable turbulences often make the effect of such measures nearly ineffective after few millimeters way.

Another essay was made with injecting the abrasive means into the jet at the nozzle outlet (U.S. Pat. No. 6,119,964). However, as foreseeable, radiation quality must strongly impaire with this measure, while regularly most efforts were made to achieve an even spray pattern, as described in DE 10 2006 015 805 A1.

Other proposals refer to sequentially cleaning the nozzle either mechanically with a tappet like in U.S. Pat. No. 4,945,688, or with a pressure surge of the medium (U.S. Pat. No. 5,312,040) or with additional liquids or filtrates (U.S. Pat. No. 5,226,565), or again with gas pressure (see above).

Moreover, it was tried to lubricate the inner wall of a nozzle of porous material by incasing it in a chamber that contains lubricants under high pressure (U.S. Pat. Nos. 5,921,456 and 6,688,947)—which might be quite intricate. Other solutions refer to a fast replaceability of nozzles (EP 0.810.038 B1, EP 0.526.087 A1, as well as U.S. Pat. Nos. 7,762,812 and 6,601,783, or to unite nozzle and mixing chamber (U.S. Pat. No. 5,114,766)—the effect of which seems questionable.

The above mentioned paradigm for past nozzle constructions—to make these from as hard a material as possible, in order to reduce their wear—was also transferred to devices with lower pressure, as far as abrasive components were applied.

However, for application with comparatively low pressure (4 to 10 bar at the nozzle) and applications of limited cleaning intensity, like e.g. the removal of biofilm these measures appear inadequately intricate—whereas particularly here the risk of clogged nozzles is quite high with water containing abrasive components. Thus, due to the high cost of adequately resistant nozzles, such cleaning equipment hitherto remained infeasible for the consumer range.

Problem to be Solved

The inventive task therefore is to find a nozzle design with regular- or low cost materials, that would avoid clogging and fast wear when applied as jet-nozzle for fluids, that contain abrasive media.

Problem Approach—Inventive Step

An actuating variable with regard to possible blockages is nozzle geometry. While it is on the one hand obvious that "dead volumes", in which deposits may adhere due to the lack of sufficiently flowing medium are to be avoided, different pressure zones and vortex reflux caused by turbulences in the narrowing of tubes can not so easily be investigated and therefore are only incompletely understood and only insufficiently representable in computer simulation. Even though these are crucial for the accumulation of blast grains at the walls of tubes and nozzles, they could sofar—without much expenditure—only be analyzed post facto from the deposits.

Due to above mentioned paradigm, institutional research for the investigation of relevant conditions related to nozzles made of hard ceramics etc., whereas the inventive approach was based on research with simple means, i.e. with nozzles from acrylic glass for in situ observation of the flow attitude.

Surprisingly it was found, that there were substantially smaller deposits and also less wear in comparison to much harder metallic nozzles with similar cross section and surface smoothness.

This was recognized to fulfil the task to implement nozzles in such an economical way, that they avoid blockages, even if its diameter is only little larger than the grain size of the firm components within the medium.

The inventive step follows the perception won from the experiments: that the material of the nozzle must have a certain flexibility on a microscopic scale, to deform itself under turbulences in a water jet of appropriate pressure, so to release accumulated particles from their walls by vibration. Besides it was found, that also the wear and tear of the nozzles is reduced, if they consist of somewhat flexible material instead of a hard one.

Both obviously is based on the fact that turbulences in the medium and periodic irregularities of the primary pressure lead to resonance effects, which release or prevent possible accumulations at the nozzle.

This is comparable to the conventional approach to employ sound generators in nozzles. However, the transmission of vibrations in hard nozzles is, due to the high periodic resonance, only effective in a very high frequency range with low amplitudes—and therefore seems to be less promising—disregard the much higher expenditure for this procedure.

SUMMARY OF THE INVENTION

One embodiment of the invention therefore comprises a nozzle made of semi-hard plastic, as is standard PMMA or PVC, which avoids expensive materials and laborious methods of manufacturing. Besides, due to their low cost, such nozzles may simply be replaced, if necessary.

Another embodiment pertains to the geometry of the nozzle: It was found that a vortex movement is favorable, that is induced proximately to the front of a compression zone and which then is led as laminarly as possibly along the sidewalls up to the nozzles orifice, which itself is bevelled at 45° within a wall thickness of 0.5 mm.

Another embodiment pertains to a nozzle for spraying media with ingredients at pressures from 4 to 10 bar, wherein the nozzle consists of semirigid plastics, like polymethylmetacrylate (PMMA) or hard PVC.

Another embodiment pertains to a nozzle for spraying media with abrasive ingredients wherein a spiral spin body is arranged before the entering of the medium into a compression zone. The spiral body may be collocated in a conical duct 25° to 45° off axis. The spiral body may contain as many turns (±1) as its maximum diameter in millimeters.

Another embodiment pertains to a nozzle for spraying media with abrasive ingredients wherein a compression zone behind an untapered spiral body constricts at 15° to 20° relative to a nozzle axis.

Another embodiment pertains to a nozzle for spraying media wherein a nozzle tube runs straight-lined between the ends of a compression zone up to an orifice outlet.

Another embodiment pertains to a nozzle for spraying media wherein the nozzle has a mouth, the mouth being tapered at 40° to 50°. The mouth may be formed within a wall thickness of not more than 1 millimeter.

Another embodiment pertains to a nozzle for spraying media having a nozzle tube, compression chamber, and expansion chamber, the nozzle tube, compression chamber, and expansion chamber each having polished walls.

Thus, in contradiction to hereditary constructions and the ideas to smoothen the stream with straight lamellae, a nozzle has been constructed, wherein twisted lamellae or a screw-type guide transform the current flow into vortices in a compression zone to enter a straight pass-way and re-expand in a bevelled orifice, thus forming a fine-spraying cone of high speed particles.

This usually could not have been done in conventional constructions, since lamellae and screw-type spiral cone usually would be clogged quite easily when applying media that contains abrasive particles of nearly the size of their keyways.

But vibrations due to the turbulences in combination with the regarded flexibility of the materials applied, obviously provoke blasts that carry it away.

DETAILED DESCRIPTION OF THE INVENTION IN DRAWINGS

Figure 2:
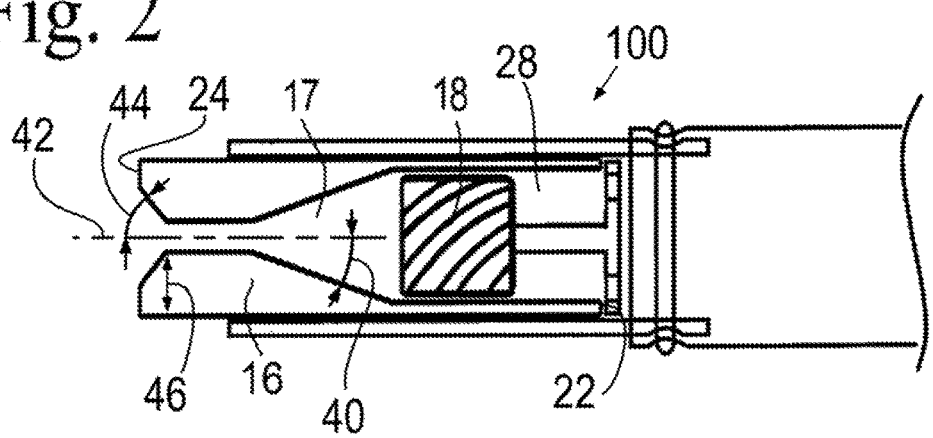

FIG. 1 illustrates an embodiment of a nozzle unit 1. FIG. 2 illustrates an embodiment of a nozzle unit 100. Each nozzle unit 1, 100 includes a like tubular body or nozzle 16. The nozzle 16 extends from an intake end 22 to a discharge end 24 spaced in a downstream direction from the intake end 22. The nozzle 16 has an annular wall 26 extending from the intake end 22 to the discharge end 24 that surrounds and defines an internal bore or duct 28 extending from the intake end 22 to the discharge end 24. The wall 26 has a constant diameter wall section 30 starting at the intake end 22 and extending to a converging conical duct or bore wall section 32. A constant diameter wall section 34 extends from the converging conical wall section 32 to a diverging or expanding conical wall section 36. The conical wall section 36 extends from the wall section 34 to the nozzle discharge end 24.

The wall section 30 defines a pressure chamber 8 in the bore or duct 28 that admits the medium into the nozzle 16. The conical wall section 32 in the bore or duct 28 defines a compression zone or compression chamber 17 that receives flow from the pressure chamber 8. The compression zone 17 extends from an upstream end of the compression zone adjacent the pressure chamber 8 to a downstream end of the compression zone adjacent the wall section 34. The compression zone 17 contracts or decreases in diameter in the downstream direction. The wall section 34 defines a straight guideway 13 that receives flow from the compression chamber 17. The conical wall section 36 defines a nozzle mouth 14 surrounding an expansion chamber 38 at the nozzle discharge 24. The expansion chamber 38 receives flow from the guideway 13 and expands in the downstream direction from the guideway 13 to the discharge end 24 of the nozzle 16.

The converging wall section 32 constricts the compression zone 17 at an angle 40 relative to a nozzle axis 42. The expanding wall section 36 expands the expansion chamber 38 at an angle 44 relative to the nozzle axis 42. The angle 44 may in embodiments be between 40 degrees and 50 degrees.

The wall thickness 46 of the nozzle 16 at the nozzle mouth 14 in embodiments may be 1 millimeter or less.

In FIG. 1 the medium enters the inlet hose 3 to be led to the nozzle unit 1, that is held in a bushing 2, by drillings or slots 7 in the terminal 6 to be led into the pressure chamber 8, where a screw-type spin body 11 having a maximum diameter dimension 48 is held by an axle 10 that leads into the conical compression chamber 17. The spin body 11 has turns 50. The spin body 11 may in embodiments contain as many turns (±1) as its maximum diameter in millimeters. The bushing 2 is held in the end portion 4 of the inlet hose 3 by a clamp 5.

The therein enclosed and through the in turning turbulence accelerated medium is pressed out through a guideway 13 into the conically bevelled orifice 14.

So particularly for the tooth cleaning with abrasive particles the jet at the nozzle mouth 14 is again expanded to form a conical spray.

FIG. 2 shows a more simply producible version with similar effect: here a cylindrical spin body of parallel twisted lamellae 18 procures the turning turbulence with which the medium with the abrasive particles enters the compression chamber 17, which—as in FIG. 1—leads through a guideway into the bevelled orifice.

List of Cited Patents

| In sucession of their citation | | | In alphabetical and nummerical order | | |
|---|---|---|---|---|---|
| No. | view PAGE | LINE No. | No. | view PAGE | LINE No. |
| 4.608.018 | 2 | 24 | DE 10 015 805 A1 | 3 | 20 |
| 4.462.803 | 2 | 25 | DE 19 640921 C1 | 3 | 13 |
| 4.482.322 | 2 | 25 | DE 19 649 921 | 3 | 10 |
| 4.540.365 | 2 | 25 | DE 3.528.137 A1 | 3 | 3 |
| 4.595.365 | 2 | 25 | DE 3.622.292 | 3 | 12 |
| 5.094.615 | 2 | 25 | EP 0-810.038 B1 | 3 | 27 |
| 5.186.625 | 2 | 25 | EP 0.258.242 B1 | 3 | 7 |
| 5.558.474 | 2 | 25 | EP 0.476.632 B1 | 2 | 38 |
| 5.733.174 | 2 | 25 | EP 0.526.087 A1 | 3 | 28 |
| 5.746.596 | 2 | 26 | EP 0.573.957 B1 | 3 | 7 |
| 5.857.851 | 2 | 26 | EP 0.691.183 B1 | 3 | 11 |
| 5.857.900 | 2 | 26 | U.S. Pat. No. 4.253.610 | 2 | 28 |
| 5.918.817 | 2 | 26 | U.S. Pat. No. 4.252.768 | 2 | 38 |
| 6.485.304 | 2 | 26 | U.S. Pat. No. 4.462.803 | 2 | 25 |
| 6.752.685 | 2 | 26 | U.S. Pat. No. 4.478.368 | 3 | 7 |
| 6.837.709 | 2 | 26 | U.S. Pat. No. 4.482.322 | 2 | 25 |
| 6.935.576 | 2 | 26 | U.S. Pat. No. 4.494.698 | 2 | 40 |
| 6.964.569 | 2 | 27 | U.S. Pat. No. 4.540.365 | 2 | 25 |
| 4.253.610 | 2 | 28 | U.S. Pat. No. 4.545.157 | 2 | 39 |
| 4.776.794 | 2 | 28 | U.S. Pat. No. 4.595.365 | 2 | 25 |
| 5.203.968 | 2 | 28 | U.S. Pat. No. 4.608.018 | 2 | 24 |
| 5.385.304 | 2 | 28 | U.S. Pat. No. 4.611.759 | 2 | 40 |
| 5.551.909 | 2 | 28 | U.S. Pat. No. 4.707.952 | 3 | 7 |
| 5.553.784 | 2 | 29 | U.S. Pat. No. 4.776.794 | 2 | 28 |
| 5.595.346 | 2 | 30 | U.S. Pat. No. 4.945.688 | 3 | 22 |
| 0.476.632 B1 | 2 | 38 | U.S. Pat. No. 5.018.317 | 3 | 8 |
| 4.252.768 | 2 | 38 | U.S. Pat. No. 5.052.624 | 2 | 39 |
| 4.545157 | 2 | 39 | U.S. Pat. No. 5.056.718 | 3 | 13 |
| 5.052.624 | 2 | 39 | U.S. Pat. No. 5.094.615 | 2 | 25 |
| 7.757.971 | 2 | 39 | U.S. Pat. No. 5.114.766 | 3 | 29 |
| 4.494.698 | 2 | 40 | U.S. Pat. No. 5.169.065 | 3 | 11 |
| 4.611.759 | 2 | 40 | U.S. Pat. No. 5.186.625 | 2 | 25 |
| 3.528.137 A1 | 3 | 3 | U.S. Pat. No. 5.203.968 | 2 | 28 |
| 5.335459 | 3 | 3 | U.S. Pat. No. 5.226.565 | 3 | 23 |
| 0.258.242 B1 | 3 | 7 | U.S. Pat. No. 5.312.040 | 3 | 22 |
| 0.573.957 B1 | 3 | 7 | U.S. Pat. No. 5.335.459 | 3 | 3 |
| 4.478.368 | 3 | 7 | U.S. Pat. No. 5.385.304 | 2 | 28 |
| 4.707.952 | 3 | 7 | U.S. Pat. No. 5.551.909 | 2 | 28 |
| 5.018.317 | 3 | 8 | U.S. Pat. No. 5.553.784 | 2 | 29 |
| 5.601.478 | 3 | 8 | U.S. Pat. No. 5.558.474 | 2 | 25 |
| 6.077.152 | 3 | 8 | U.S. Pat. No. 5.595.346 | 2 | 30 |
| 6.842.453 | 3 | 8 | U.S. Pat. No. 5.601.478 | 3 | 8 |
| 6.846.211 | 3 | 8 | U.S. Pat. No. 5.733.174 | 2 | 25 |
| 19 649 921 | 3 | 10 | U.S. Pat. No. 5.746.596 | 2 | 26 |
| 0.691.183 B1 | 3 | 11 | U.S. Pat. No. 5.857.851 | 2 | 26 |
| 5.169.065 | 3 | 11 | U.S. Pat. No. 5.857.900 | 2 | 26 |
| 3.622.292 | 3 | 12 | U.S. Pat. No. 5.918.817 | 2 | 26 |
| 19 640921 C1 | 3 | 13 | U.S. Pat. No. 5.921.465 | 3 | 26 |
| 5.056.718 | 3 | 13 | U.S. Pat. No. 6.752.685 | 2 | 26 |
| 6.119.964 | 3 | 18 | U.S. Pat. No. 6.077.152 | 3 | 8 |
| 10 015 805 A1 | 3 | 20 | U.S. Pat. No. 6.119.964 | 3 | 18 |
| 4.945.688 | 3 | 22 | U.S. Pat. No. 6.485.304 | 2 | 26 |
| 5.312.040 | 3 | 22 | U.S. Pat. No. 6.601.783 | 2 | 28 |
| 5.226.565 | 3 | 23 | U.S. Pat. No. 6.688.947 | 3 | 26 |
| 5.921.465 | 3 | 26 | U.S. Pat. No. 6.837.709 | 2 | 26 |
| 6.688.947 | 3 | 26 | U.S. Pat. No. 6.842.453 | 3 | 8 |
| 0-810.038 B1 | 3 | 27 | U.S. Pat. No. 6.846.211 | 3 | 8 |
| 0.526.087 A1 | 3 | 28 | U.S. Pat. No. 6.935.576 | 2 | 26 |
| 7.762.812 | 3 | 28 | U.S. Pat. No. 6.964.569 | 2 | 27 |
| 6.601.783 | 2 | 28 | U.S. Pat. No. 7.757.971 | 2 | 39 |
| 5.114.766 | 3 | 29 | U.S. Pat. No. 7.762.812 | 3 | 28 |

What is claimed is:

1. A nozzle unit for a dental apparatus that discharges a water stream carrying abrasive particles, the nozzle unit comprising:

a one-piece nozzle, a spin body, and a member attaching the spin body to the nozzle;

the nozzle being formed of a semirigid plastic, the nozzle comprising an intake end, a discharge end, and a duct surrounded by a duct wall extending in a downstream direction along an axis of the nozzle from the intake end to the discharge end, the axis defining a circumferential direction around the axis, the discharge end configured to discharge fluid from the nozzle, the nozzle being sufficiently flexible to release accumulated particles on the duct wall when a water stream flows through the duct; and the spin body being a solid body comprising a closed first end, a closed second end spaced in the downstream direction from the second end, and an outer first surface extending from the first end to the second end of the spin body, the first surface being spaced away from the axis and surrounding the axis, the spin body being disposed in the duct and being configured to generate vortexal flow in water flowing in the duct past the spin body;

the member having opposite first and second ends, the member being disposed in the duct, the first end of the member being attached to and extending away in an upstream direction from the first end of the spin body to the second end of the member, the second end of the member being connected to the nozzle upstream from the spin body, the member between said first end and said second ends of the member being spaced away from the duct wall wherein the member and the duct wall cooperatively form a first channel portion extending along the duct wall in the downstream direction and surrounding the member;

the spin body being spaced away from the duct wall wherein the outer surface of the spin body and the duct wall cooperatively form therebetween a second channel portion extending downstream from the first channel portion along the duct wall from the first end of the spin body to the second end of the spin body, the second channel portion surrounding the spin body and the second channel portion being surrounded by the duct wall, the spin body comprising at least one second surface extending away from the first surface into the second channel portion, the at least one second surface extending in the circumferential direction at least partially around the first surface;

the spin body obstructing downstream water flow past the spin body wherein all of the water in the water stream flowing through the nozzle flows through the first channel portion and the second channel portion and around the entire outer first surface of the spin body when the water stream flows past the spin body, the water stream when flowing through the second channel portion engaging the at least one second surface and being urged by the at least one second surface to flow with a circumferential flow component and thereby generate vortexal flow of the water stream downstream from the spin body.

2. The nozzle unit of claim 1 wherein a first portion of the duct wall defines an expanding nozzle mouth at the discharge end of the nozzle, the nozzle mouth expanding in the downstream direction, the nozzle mouth being tapered at between 45° and 50°.

3. The nozzle unit of claim 2 wherein the first portion of the duct wall has a maximum wall thickness of not greater than 1 millimeter.

4. The nozzle unit of claim 2 wherein a second portion of the duct wall defines a straight guideway that discharges into the nozzle mouth.

5. The nozzle unit of claim 1 wherein the nozzle is formed from polymethylmetacrylate (PMMA) or hard PVC.

6. The nozzle unit of claim 1 wherein the member comprises an outer surface surrounding the axis, the outer surface of the member being closer to the axis than the outer first surface of the spin body.

7. The nozzle unit of claim 1 wherein the spin body is an untapered spin body.

8. The nozzle unit of claim 1 wherein the duct wall defines a compression zone in a portion of the duct, the compression zone extends in the downstream direction and constricts as the compression zone extends in the downstream direction, and the spin body is an untapered spin body disposed outside of the compression zone.

9. The nozzle unit of claim 8 wherein the compression zone constricts at between 15° and 20° off axis.

10. The nozzle unit of claim 1 further comprising a stream of water flowing into the intake end of the nozzle and being discharged from the discharge end of the nozzle, the pressure of the stream being at or below 10 bar at the intake end, the stream of water carrying abrasive particles suitable for dental cleaning through the nozzle, the abrasive particles being discharged from the nozzle at the discharge end of the nozzle.

11. The nozzle of claim 1 wherein the at least one second surface comprises a plurality of second surfaces, the plurality of second surfaces being parallel with one another.

12. The nozzle of claim 1 wherein the spin body comprises twisted lamellae, the at least one second surface comprises a plurality of second surfaces, and each second surface of the plurality of second surfaces is disposed on a respective lamella.

13. The nozzle unit of claim 1 wherein the spin body is a tapered spin body.

14. The nozzle unit of claims 13 wherein the duct wall defines a compression zone in a portion of the duct, the compression zone extends in the downstream direction and constricts as the compression zone extends in the downstream direction, and the spin body is at least partially disposed in the compression zone.

15. The nozzle unit of claim 14 wherein the compression zone constricts at between 25 degrees and 45 degrees off axis.

16. A nozzle for discharging a stream of water carrying abrasives for dental cleaning, the nozzle comprising:

a tubular body formed of semirigid plastic and comprising an intake end, a discharge end spaced downstream from the intake end, an annular wall extending from the intake end to the discharge end, the wall defining and surrounding a duct extending along an axis in a downstream direction through the tubular body from the intake end to the discharge end, a first portion of the wall defining a compression zone in the duct having an upstream end and a downstream end spaced in the downstream direction from the upstream end, the compression zone contracting in the downstream direction from the upstream end to the downstream end of the compression zone; and a spin body in the duct, the spin body configured to generate vortexal flow in a stream of water in the duct flowing past the spin body, the spin body having a closed first end, an opposite closed second end disposed downstream from the first end, and an outer first surface extending from the first end to the second end, the first surface spaced away from the axis and surrounding the axis, the spin body disposed in the duct in an upstream direction from the downstream end of the compression zone, the spin body and the wall cooperatively defining a first channel portion between the spin body and the wall extending from the first end of the spin body to the second end of the spin body, the first channel portion surrounding the first surface of the spin body and being surrounded by the wall;

the spin body comprising at least one second surface extending away from the first surface into the first channel portion, the at least one second surface extending in the circumferential direction at least partially around the first surface;

a member in the duct having opposite first and second ends, the member connecting the spin body and the tubular body, the first end of the member attached to an upstream side of the spin body and extending from the spin body in an upstream direction to the second end of the member, the second end of the member being connected to the tubular body upstream from the spin body, the member between the first and second ends of the member being spaced away from the wall wherein the member and the duct wall cooperatively form a second channel portion extending along the duct upstream from the first channel portion and surrounding the member;

wherein all of the water in the water stream flowing through the duct flows through the second channel portion and the first channel portion when the water stream flows past the spin body, all of the water flowing through the first channel portion surrounding the spin body and flowing between the outer first surface of the spin body and the wall, the water flowing through the first channel portion engaging the at least one second surface of the spin body, the at least one second surface being disposed on the first surface of the spin body to induce a circumferential flow component in the water flowing through the first channel portion and thereby generate vortexal flow in the water flowing past the spin body.

17. The nozzle of claim 16 wherein the spin body is disposed outside of the compression zone.

18. The nozzle unit of claim 17 wherein the compression zone extends along an axis, and the compression zone constricts at between 15° to 20° off axis.

19. The nozzle unit of claim 17 wherein the spin body is an untapered spin body.

20. The nozzle of claim 16 wherein the spin body has a maximum diameter of N mm and the at least one second surface is a spiral surface having between N+1 and N−1 turns.

21. The nozzle of claim 16 wherein the plastic is polymethylmetacrylate (PMMA) or hard PVC.

22. The nozzle of claim 16 wherein the wall comprises a second portion defining a guideway in the duct, the guideway extending along a straight line downstream from the compression zone.

23. The nozzle of claim 16 wherein the wall comprises a second wall portion defining an expansion zone in the duct downstream from the compression zone, the expansion zone having an upstream end and a downstream end spaced downstream from the upstream end, the downstream end of the expansion zone located at the downstream end of the body, the expansion zone expanding in the downstream direction.

24. The nozzle of claim 23 wherein the expansion zone extends along an axis and the expansion chamber expands at between 40° and 50° off axis.

25. The nozzle of claim 23 wherein the wall comprises a third wall portion connecting the first and second wall portions, the third wall portion defining a guideway in the duct extending in a straight line from the compression zone to the expansion zone.

26. The nozzle of claim 25 wherein the guideway has a uniform diameter from the compression zone to the expansion zone.

27. The nozzle of claim 25 wherein the first wall portion, second wall portion, and third wall portion are polished.

28. The nozzle of claim 23 wherein the second wall portion has a wall thickness of not more than 1 mm.

29. The nozzle of claim 16 wherein the spin body is outside of the compression zone and comprises a plurality of twisted lamellae, the at least one second surface comprises a plurality of second surfaces, each second surface of the plurality of second surfaces being disposed on a respective one of the lamellae.

30. The nozzle unit of claim 16 wherein the member has an outer surface disposed along the axis, the outer surface of the member being closer to the axis than the outer first surface of the spin body.

31. The nozzle of claim 16 further comprising a stream of water flowing into the intake end of the nozzle and being discharged from the discharge end of the nozzle, the pressure of the stream being at or below 10 bar at the intake end, the stream of water carrying abrasive particles suitable for dental cleaning through the nozzle, the abrasive particles being discharged from the nozzle at the discharge end of the nozzle.

32. The nozzle of claim 16 wherein the spin body is disposed in the compression zone.

33. The nozzle of claim 32 wherein the compression zone extends along an axis, and the compression zone constricts at between 25 degrees and 45 degrees off axis.

34. The nozzle of claim 23 wherein the spin body is a tapered spin body.

* * * * *